United States Patent
Zahoor et al.

(10) Patent No.: US 6,184,428 B1
(45) Date of Patent: Feb. 6, 2001

(54) CATALYST AND PROCESS FOR ETHYLENE OLIGOMERIZATION

(75) Inventors: Mohammad Akhtar Zahoor; Fahad Al-Sherehy, both of Riyadh (SA); Olagoke Olabisi, Houston, TX (US); Mohammed M. Abdillahi; Mian Rahat Saeed, both of Dhahran (SA)

(73) Assignee: Saudi Basic Industries Corporation (SA)

( * ) Notice: Under 35 U.S.C. 154(b), the term of this patent shall be extended for 0 days.

(21) Appl. No.: 09/251,540

(22) Filed: Feb. 17, 1999

Related U.S. Application Data

(60) Provisional application No. 60/082,654, filed on Apr. 22, 1998.

(51) Int. Cl.⁷ .................. C07C 2/26; C07C 2/32; C07C 2/36; B01J 31/02; B01J 31/24
(52) U.S. Cl. .................. 585/523; 585/525; 585/527; 585/528; 585/529; 585/531; 502/155; 502/162
(58) Field of Search .................. 585/523, 527, 585/528, 529, 531, 525; 502/155, 162

(56) References Cited

U.S. PATENT DOCUMENTS

| | | | |
|---|---|---|---|
| 3,532,765 | 10/1970 | Barnett et al. | 585/511 |
| 3,644,564 | 2/1972 | van Zwet et al. | 585/520 |
| 3,676,523 | 7/1972 | Mason | 585/523 |
| 3,725,306 * | 4/1973 | Yoo | 502/161 |
| 3,737,475 * | 6/1973 | Mason | 585/523 |
| 3,758,558 * | 9/1973 | Mason et al. | 562/405 |
| 3,825,615 * | 7/1974 | Lutz | 585/523 |
| 4,293,725 | 10/1981 | Beach et al. | 585/523 |
| 4,472,525 * | 9/1984 | Singleton | 502/155 |
| 4,482,640 | 11/1984 | Knudsen et al. | 502/155 |
| 4,503,280 * | 3/1985 | Singleton | 585/527 |
| 4,518,814 | 5/1985 | Knudsen et al. | 585/523 |
| 4,528,416 | 7/1985 | Lutz | 585/527 |
| 4,628,138 | 12/1986 | Barnett et al. | 585/531 |
| 4,689,437 | 8/1987 | Murray | 585/526 |
| 5,286,696 | 2/1994 | Wu | 502/155 |

FOREIGN PATENT DOCUMENTS

D-177999  10/1985  (EP) .

* cited by examiner

*Primary Examiner*—Walter D. Griffin
(74) *Attorney, Agent, or Firm*—Akin, Gump, Strauss, Hauer & Feld, LLP

(57) ABSTRACT

A catalyst and a process are provided for oligomerizing ethylene. A heterogeneous catalyst system comprises: (1) a chelating ligand, preferably 2-diphenyl phosphino benzoic acid (DPPBA); (2) a nickel precursor, preferably nickel chloride hexahydrate ($NiCl_2.6H_2O$); (3) a catalyst activator, preferably sodium tetraphenylborate ($NaBPh_4$); and (4) silica. A 1:1:1 molar ratio of Ni:DPPBA:$BPh_4$ catalyst components are fixed on a silica support using low-temperature fixation. The catalyst components are dispersed in a diluent, preferably ethanol, and silica is added. The ethanol is evaporated using freeze-drying equipment to form a silica-supported catalyst system. The silica-supported catalyst is slurried in ethanol in a reactor, and ethylene is added. The reactor pressure and temperature are maintained at about 725 psig and 100° C., respectively, for about two hours. The oligomer product formed has a narrower weight percent distribution, typically having about 96 weight percent $C_4$'s to $C_{10}$'s, compared to product formed using a homogeneous catalyst system.

24 Claims, No Drawings

CATALYST AND PROCESS FOR ETHYLENE OLIGOMERIZATION

CROSS-REFERENCE TO RELATED APPLICATIONS

This application claims the benefit of and priority to U.S. Provisional Application No. 60/082,654, filed Apr. 22, 1998, having the same title as the present patent application.

STATEMENT REGARDING FEDERALLY SPONSORED RESEARCH

Not applicable.

BACKGROUND OF THE INVENTION

1. Field of the Invention

The present invention relates to ethylene oligomerization to produce alpha-olefins, and in particular, to a heterogeneous catalyst and a process for ethylene oligomerization.

2. Description of the Related Art

An oligomer is a multiple unit of a monomer, and in this case the monomer of interest is ethylene. Oligomers include dimers, trimers, tetramers, and so on, but the resulting molecule is smaller than a polymer. Oligomers of ethylene are linear alpha-olefins which typically contain between 4 and 20 carbon atoms. Linear alpha-olefins are commercially important, and thus, improvements in the production of linear alpha-olefins are highly desirable.

In U.S. Pat. No. 3,676,523, issued to Mason on Jul. 11, 1972, Mason discloses a process of oligomerizing ethylene to linear alpha-olefins by reacting ethylene in a liquid phase solution in the presence of a nickel catalyst. Mason describes reacting nickel chloride hexahydrate, sodium borohydride and a potassium salt of a dihydrocarbylphosphinobenzoic acid, such as o-diphenylphosphinobenzoic acid, in a reaction medium of 1,4-butanediol and ethylene. Thus, Mason discloses a homogeneous catalyst and a process of oligomerizing ethylene in the presence of the catalyst in a polar organic solvent. The process is characterized by ethylene conversion to a linear alpha olefin product mixture of relatively high proportion of olefinic products in a higher molecular range including $C_{12}$–$C_{20}$ alpha-olefins.

Lutz, the inventor of U.S. Pat. No. 4,528,416 issued Jul. 9, 1985, disclosed a process for producing ethylene oligomers in a polar organic solvent in the presence of a catalyst which is a chelate of nickel with a bidentate ligand. The solvent mixture contained between about 40 and 82% by weight of an aliphatic dihydric alcohol and between about 18 and 60% by weight of an aliphatic monohydric alcohol. It is critical to the Lutz process that the ethylene partial pressure be at least about 800 psig. Lutz stated that the use of the described reaction solvent mixture resulted in improvement in the rate of ethylene oligomerization and/or modification of the carbon number distribution of the product oligomer mixture. Lutz states that it is essential that the catalyst composition be prepared in the presence of ethylene, and the ethylene should be at a substantially elevated pressure, preferably in the range from 400 to 1,500 psig. The catalyst of Lutz is homogeneous, and it is necessary to carry out the oligomerization process in the solvent described above.

Wu in U.S. Pat. No. 5,286,696, issued Feb. 15, 1994, describes a heterogeneous catalyst. Wu states that homogeneous catalyst systems, such as described above, are not suitable for continuous processes or are relatively expensive. Wu further states that the ethylene oligomerization processes known at that time had not always achieved high catalyst productivity and good product selectivity. Wu discloses an ethylene oligomerization process comprising: (1) combining a nickel compound and a phosphine compound and a solvent to form a mixture; (2) combining this mixture with a phosphated alumina under an ethylene pressure to form a catalyst system; (3) contacting ethylene with the catalyst system under oligomerization conditions to produce higher olefins having more than 2 carbon atoms; and (4) recovering the higher olefins. Wu states that an advantage of his invention is the use of a heterogeneous composition that is easily employed in a continuous process for ethylene oligomerization.

Thus, a heterogeneous catalyst system, such as where the catalyst is a solid suspended in a liquid diluent, is advantageous for a continuous process, which can have a higher production rate than a batch process. Further, it remains true that even slight improvements in the process and/or catalyst for making ethylene oligomers is highly desirable because there is a significant commercial demand for linear alpha-olefins, such as produced by ethylene oligomerization.

SUMMARY OF THE INVENTION

The present invention provides a catalyst on a solid support slurried in a diluent to provide a heterogeneous catalyst system. Thus, the present invention is advantageous for a continuous process. The catalyst system of the present invention is highly active for ethylene oligomerization and is capable of selectively producing a desirable distribution of linear alpha-olefins. For product produced using the present invention, the product distribution is generally narrower than a product distribution obtained from a homogeneous catalyst system. Further, the catalyst system of the present invention is stable in air and can be stored for a period of time before use.

In one aspect, the present invention provides a process for ethylene oligomerization. A supported nickel catalyst is maintained as a slurry in a liquid material. The preferred catalyst is a reaction product of 2-diphenylphosphino benzoic acid (DPPBA), nickel chloride hexahydrate ($NiCl_2.6H_2O$) and sodium tetraphenylborate, which is deposited upon silica particles by freeze-dry evaporation of an alcohol solvent. Ethylene feed is dissolved into the liquid material, and catalyst slurry temperature is controlled from about 80° C. to about 120° C. for a time sufficient to oligomerize the ethylene to produce lower alpha-olefins.

In another aspect, the present invention provides the catalyst for the ethylene oligomerization process. DPPBA, $NiCl_2.6H_2O$ and sodium tetraphenylborate are reacted together in a solvent to form a complex in a solution. Preferably, an alcohol is used as the solvent. A support material, preferably silica, is added to the solution, which is then fed into freeze-drying equipment. At a low temperature, the solvent is evaporated, and the catalyst reaction product is deposited onto the support material, thus forming the heterogeneous catalyst.

DETAILED DESCRIPTION OF THE INVENTION

The ethylene oligomers produced by the process of the present invention are addition products that contain two or more ethylene units, but not as many as ethylene units as in the relatively high molecular weight addition product referred to as polyethylene. The present invention is particularly adapted for production of linear mono-olefinic oligomers, particularly alpha-olefins having from 4 to about 20 carbon atoms. For all that they teach about the oligomerization process in general, including catalyst therefor, U.S. Pat. Nos. 3,676,523; 4,528,416; and 5,286,696, the patents described in the background section, are incorporated by reference in their entirety.

The catalyst system of the present invention is based on the following four components: (1) a chelating ligand; (2) a nickel precursor; (3) an activator; and (4) a support, preferably silica. Generally, the chelating ligand is a dihydrocarbylphosphinobenzoic acid such as described in U.S. Pat. No. 3,676,523. However, in a preferred catalyst system, the chelating ligand is 2-diphenyl phosphino benzoic acid (DPPBA). DPPBA is commercially available from Institute of Petroleum Chemistry, Aachen, Germany.

The nickel precursor can, in general, be prepared from many nickel salts including both inorganic and organic nickel salts. Simple divalent nickel salts are employed for preparing the catalyst composition of the present invention. Simple divalent nickel salts contain water of crystallization, a hydrate, in addition to bondingly coordinated anionic groups. Although, it is believed that any one of numerous nickel salts can be used, a complex must be formed between the catalyst components. The nickel precursor presently preferred is nickel chloride hexahydrate ($NiCl_2 \cdot 6H_2O$).

The activator can be any compound that sufficiently activates the catalyst to provide the desired oligomerization. Various catalyst activators have been used in the past. Suitable activators are generally capable of transferring a hydride or an alkyl, alkenyl, alkynyl, or aryl group from itself to the metal/ligand complex formed by the reaction of the metal salt with the ligand, and thus bonding the group to the transition metal. Useful activators include borohydrides, aryl boranes, borates, organoaluminum compounds, boron compounds and organozinc compounds. U.S. Pat. No. 4,689,437 issued to Murray on Aug. 25, 1987, provides an extensive discussion of catalyst activators and is incorporated by reference in its entirety. Sodium tetraphenylborate ($NaBPh_4$) is the preferred catalyst activator of the present invention. As compared to other catalyst activators, sodium tetraphenylborate is believed to provide the most active catalyst system.

Catalyst Preparation

The catalyst system is prepared by mixing and dispersing predetermined amounts of the chelating ligand, the nickel precursor and the catalyst activator in a solvent. Ethanol is the preferred solvent, but suitable solvents include water, monohydric and dihydric alcohols, ethers, such as diethyl ether, ketones, such as acetone and methyl ethyl ketone, tetrahydrofuran and acetic acid. Although the amounts can be varied, the preferred molar ratio of catalyst components in the catalyst system is 1:1:1 for nickel:DPPBA:tetraphenylborate. The catalyst solution is stirred for a period of time until a complex is formed between the catalyst components. If the solvents were removed, the reaction complex would assume a liquid form.

Complex formation is indicated by a change in color, a yellow orange color indicating that a complex has been formed. A predetermined amount of a solid dehydrated support is added to the catalyst solution in a controlled environment. Various catalyst supports can be used, and typically, a solid inorganic oxide support is preferred. The catalyst support can include one or more metal oxides, such as oxides of silica or alumina. Molecular sieves and acid-treated clays can be used, and these can be naturally occurring or man made. The preferred support for this invention is silica. The amount of silica employed is such as to provide a loading of nickel thereon of about 2 to about 4.5 weight percent of the total solids on a dry basis, and more preferably a nickel loading of about 3.4 weight percent.

The solvent is removed from the catalyst solution to fix the catalyst on the support. Any suitable method for removing the solvent so that the remaining catalyst components are deposited on the support can be used. However, the solvent is preferably evaporated, and preferably, at low temperatures. In a preferred embodiment the catalyst solution is subjected to freeze drying for low temperature fixation of the catalyst onto the support. The catalyst is preferably fixed to a silica support using freeze-drying equipment operating between $-60°$ C. and $-70°$ C. While inside the freeze-drying equipment, the catalyst solution can be subjected to very low heating under vacuum to speed up the solvent evaporation process. A condenser can be used to capture solvent vapors by operating the condenser at a lower temperature than the freeze-drying equipment. For example, the condenser might operate between $-75°$ C. and $-85°$ C.

The solvent removal process is continued until complete so that a powdery supported catalyst system remains. Unlike some catalyst systems used in the past for oligomerization of ethylene, the supported catalyst system of the present invention is stable in air. Further, the supported catalyst system can be stored for a period of time before use if stored in an inert atmosphere, such as argon. The silica-supported catalyst system of the present invention can be stored as prepared in an argon atmosphere for a period of up to about 7 days without any loss in catalyst activity.

Process

The catalyst, prepared as described above, is used in a process to oligomerize ethylene. A predetermined amount of the silica supported catalyst is charged to a reactor and slurried in a specific amount of a diluent. Suitable diluents include those diluents that are described above with reference to making a catalyst solution, and the same diluent used for making the catalyst solution can be used for slurrying the silica supported catalyst. Alternatively, a different diluent can be used if desired. The catalyst concentration of nickel in the slurry is preferably maintained in a range from about 0.8 to about 1.2 mmole/liter. The supported catalyst should be well dispersed in the diluent, which can be accomplished using an agitator. The slurry of the supported catalyst in the diluent is preferably maintained at a temperature of from about 80° C. to about 120° C.

Ethylene is charged to the reactor and mixed with the diluent containing the silica-supported catalyst. The pressure in the reactor is preferably maintained between about 290 psig and about 725 psig. Oligomers, such as dimers, trimers, tetramers, and pentamers, are formed as the ethylene reacts in the presence of the silica-supported catalyst. The reaction time ranges between about 2 and 3 hours with the preferred reaction time being about 2 hours. During the oligomerization reaction, the nickel is preferably maintained at a concentration of 0.8 mmole Ni/liter; the temperature is maintained preferably at about 100° C.; and the pressure is maintained at preferably about 725 psig. When using ethanol as a diluent for slurrying the silica supported catalyst, the solubility of the ethylene in ethanol at 4,000 kPa and 100° C. is about 0.554 moles of ethylene per mole of ethanol.

The oligomerization reaction is preferably carried out in a slurry loop reactor with a continuous feed of ethylene. Slurry is continuously withdrawn from the reactor and fed to a flash drum. Product oligomers are flashed overhead and further separated by fractional distillation. A bottoms product is withdrawn from the flash drum and contains the silica supported catalyst, the diluent and any heavy oligomers that did not flash overhead. The bottoms product is filtered to recover the silica support catalyst, which is then reslurried with fresh and/or recycled diluent, with make-up catalyst added as necessary, and recycled to the reactor. The filtrate is processed to separate and recover diluent and heavy oligomers. The recovered diluent can be used to reslurry the silica supported catalyst.

This process and heterogeneous catalyst system therefor oligomerizes the ethylene to linear alpha-olefins. The olefins thus produced are dissolved in the diluent in which the catalyst is slurried and are removed by flashing or fractionation, with unreacted ethylene so recovered being recycled as feed to the oligomerization reactor. The oligomers can be further separated and recovered by fractional distillation. This catalyst system is exceedingly active for ethylene oligomerization, and it is capable of selectively producing a desired profile of linear alpha-olefin products.

The weight percent oligomer product distribution formed using the heterogeneous catalyst system described above produces a generally narrower distribution of oligomer products as compared to oligomer products produced in a homogeneous catalyst system. The oligomer product distribution for the catalyst system of the present invention is about 96% by weight $C_4$'s to $C_{10}$'s. In comparison the product distribution for a homogeneous catalyst solution is about 88% by weight $C_4$'s to $C_{10}$'s. The catalyst activity, the conversion to linear alpha-olefins, and the narrower weight percent distribution are all better than that obtained in prior art catalyst systems, particularly those using homogeneous catalyst systems. The silica-supported catalyst of the present invention is stable in air and can be stored as prepared under argon for a shelf life of up to seven days.

EXAMPLE

Weighed amounts of DPPBA, $NiCl_2.6H_2O$, and $NaBPh_4$ (0.4194 gm, 0.3214 gm and 0.4633 gm, respectively) were placed in a glass flask, and about 100 ml ethanol was added. The solution was stirred for about 45 minutes. A yellow orange color developed which indicates the complex formation between the catalyst components. Calcined Grace-1356 silica support (4.1 gm) was added under argon. This mixture was stirred for another 40 minutes before being transferred to freeze-drying equipment for low temperature fixation. The mixture of DPPBA, $NiCl_2.6H_2O$, $NaBPh_4$, and the silica support in ethanol was placed inside the freeze-drying chamber and then cooled to −65° C. The mixture was then subjected to very low heating under vacuum in order to speed up the ethanol evaporation process. The migrating vapors of ethanol were trapped inside a condenser, which was set at a temperature of −80° C. This process was continued until the ethanol was completely evaporated leaving a powdery supported catalyst system.

The supported catalyst (63 mg) was weighed in a Schlenk flask with a magnetic stirrer bar and slurried in distilled ethanol (20 ml) to give a desired concentration of 0.8 mmole/L in a reactor. The slurry was stirred for about 15 minutes. The content of the Schlenk flask was transferred into the reactor (20 ml slurry for a 75 ml reactor and 60 ml slurry for a 300 ml reactor) via a syringe with a long plastic needle of ⅛ inch OD. The valve was closed, and the reactor was disconnected from the argon line. The content of the reactor was weighed, and high purity ethylene gas was fed from a cylinder into the reactor.

The reactor was charged to a pressure of 725 psig with ethylene. Time was allowed for the dissolution of gas in the solvent before stopping the feed. The reactor was weighed before being heated to and maintained at 100° C., the oligomerization reaction temperature. The pressure drop due to the oligomerization reaction was carefully monitored. The oligomerization reaction was terminated after 120 min or 180 min. The reactor was then weighed. The unreacted ethylene gas from the reactor was passed through a trap at −40° C. to collect all the butene and hexene products coming with unreacted ethylene. By weighing the reactor content at each step of the experiment, all the calculations of conversion, turn over number, and activity were accurately made from the mass, and the results are summarized in Table 1.

TABLE 1

| Run # | Time (min) | Activity | Conv. (%) | TON | Weight Percent distribution of LAO (Linearity %) | | | |
|---|---|---|---|---|---|---|---|---|
| | | | | | $C_4$ | $C_6$ | $C_8$ | $C_{10}$ |
| 1 | 120 | 1863 | 49 | 7813 | 31 (99.9) | 33 (99.2) | 19 (98.2) | 13 (96.9) |
| 2 | 180 | 1526 | 59 | 9598 | 35 (98.7) | 31 (98.1) | 16 (97.4) | 12 (95.3) |

Definitions:

Conversion (%)=Weight of ethylene reacted (gm)/Weight of ethylene fed (gm)×100

Activity=Weight of ethylene reacted (gm)/Weigh of Ni (gm)×time (hr.)

TON=Turn over number=moles of ethylene reacted per mole of Ni in the catalyst

Linearity of LAO product (%)=Linear α-olefin content/Total olefin having same carbon number×100

As can be seen in the data of Table 1, the catalyst and process of the present invention provides favorable results. In the first run the reaction was carried out for two hours, and forty-nine percent of the ethylene feed was converted to linear alpha-olefins (LAO). The catalyst activity was 1,863 gm of ethylene reacted per gram of nickel per hour and the turn over number (TON) was 7,813 moles of ethylene reacted per mole of nickel in the catalyst.

Of the product obtained, 96 weight percent was linear alpha-olefins in the $C_4$ to $C_{10}$ range. Dimers and trimers were selectively produced, accounting for 31 and 33 weight percent, respectively, of the final product. The $C_4$ dimers were 99.9% 1-butene, and the $C_6$ trimers were 99.2% 1-hexene. The $C_8$ tetramers accounted for 19% of the product and were 98.2% 1-octene. The $C_{10}$ pentamers accounted for 13 weight percent of the product and was 96.9% 1-decene. Thus, a high proportion (96 weight percent) of the oligomerization product formed according to the present invention in the first run was lower-weight linear alpha-olefins in the range of $C_4$ to $C_{10}$. Sixty-four percent of the oligomerization product was in the $C_4$ to $C_6$ range, and 83% was in the $C_4$ to $C_8$ range.

In the second run the reaction was carried out for three hours and achieved a conversion of 59 weight percent of the ethylene feed to linear alpha-olefins. The catalyst activity in the second run was lower than that in the first run at 1,526 gm of ethylene per gm of nickel per hour. However, the turnover number was higher in the second run with 9,598 moles of ethylene reacted per mole of nickel in the catalyst. In the second run 94 weight percent of the product was linear alpha-olefins in the $C_4$ to $C_{10}$ range, as compared to 96 weight percent in the first run. Of the final product about 35 weight percent was $C_4$ dimers of which about 98.7% was 1-butene. About 31% of the final product was $C_6$ trimers of which about 98.1% was 1-hexene. The lower-weight dimers, trimers and tetramers accounted for 82 weight percent of the final product. The $C_8$ tetramers were 16 weight percent of the final product of which about 97.4% was 1-octene.

Thus, it can be seen that the heterogeneous catalyst system of the present invention selectively dimerizes, trimerizes, tetramerizes and pentamerizes ethylene to linear alpha-olefins in the $C_4$ to $C_{10}$ range. In the first run the $C_4$ to $C_{10}$ components comprised 96 weight percent of the final product, and in the second run the $C_4$ to $C_{10}$ components comprised 94 weight percent of the final product. Thus, the heterogeneous catalyst system of the present invention is useful for producing lower-weight linear alpha-olefins.

One embodiment of the present invention is thus described in reasonable detail, but one skilled in the art will recognize that variations and modifications can be affected which are within the spirit and scope of the invention as described and defined in the following claims.

We claim:

1. A process for ethylene oligomerization, comprising the steps of:
    maintaining a supported nickel catalyst as a slurry in a liquid material; said supported nickel catalyst consisting of a reaction product of 2-diphenylphosphino benzoic acid (DPPBA), nickel chloride hexahydrate ($NiCl_2.6H_2O$) and sodium tetraphenylborate deposited upon silica particles;
    dissolving ethylene into the liquid material of said supported nickel catalyst slurry;
    controlling said slurry temperature from about 80° C. to about 120° C. for a time sufficient to oligomerize ethylene to produce lower alpha-olefins.

2. The process of claim 1, wherein the catalyst is maintained at a concentration between about 0.8 mmole of nickel per liter of liquid material and about 1.2 mmole of nickel per liter of liquid material.

3. The process of claim 1, wherein the catalyst is maintained at a concentration of about 0.8 mmole of nickel per liter of liquid material.

4. The process of claim 1, wherein the temperature is maintained at about 100° C.

5. The process of claim 1, wherein the ethylene is maintained at a pressure between about 290 psig and about 725 psig.

6. The process of claim 1, wherein the ethylene is maintained at a pressure of about 725 psig.

7. The process of claim 1, wherein the molar ratio of nickel:DPPBA:tetraphenylborate is about 1:1:1.

8. The process of claim 1, wherein the loading of nickel on silica ranges between about 2 weight percent and about 4.5 weight percent.

9. The process of claim 1, wherein the loading of nickel on silica is about 3.4 weight percent.

10. The process of claim 1, wherein the liquid material is selected from the group consisting of monohydric alcohols, dihydric alcohols, ketones, ethers, acetic acid, tetrahydrofuran, toluene, xylenes and hexanes.

11. The process of claim 1, wherein the liquid material is ethanol.

12. The process of claim 1, wherein ethylene is dissolved in the liquid material in a concentration of about 0.55 mmole of ethylene per mole of the liquid material.

13. The process of claim 1, wherein the liquid material is ethanol and the conditions are such that about 0.55 moles of ethylene is dissolved in one mole of ethanol.

14. The process of claim 1, wherein $C_4$'s to $C_{10}$'s comprise about 96 weight percent of the alpha-olefins produced.

15. The process of claim 1, wherein the slurry is maintained under an argon atmosphere.

16. A catalyst for ethylene oligomerization, comprising:
    a supported nickel catalyst consisting of a reaction product of 2-diphenyl phosphino benzoic acid (DPPBA), a nickel precursor and a catalyst activator deposited upon silica particles from an alcohol solution by freeze-dry evaporation of said alcohol.

17. A catalyst for ethylene oligomerization, comprising:
    a supported nickel catalyst consisting of a reaction product of 2-diphenyl phosphino benzoic acid (DPPBA), nickel chloride hexahydrate ($NiCl_2.6H_2O$) and a catalyst activator deposited upon silica particles from an alcohol solution by freeze-dry evaporation of said alcohol.

18. A catalyst for ethylene oligomerization, comprising:
    a supported nickel catalyst consisting of a reaction product of 2-diphenyl phosphino benzoic acid (DPPBA), a nickel precursor and a sodium tetraphenylborate ($NaBPh_4$) deposited upon silica particles from an alcohol solution by freeze-dry evaporation of said alcohol.

19. A catalyst for ethylene oligomerization, comprising:
    a supported nickel catalyst consisting of a reaction product of 2-diphenylphosphino benzoic acid (DPPBA), nickel chloride hexahydrate ($NiCl_2.6H_2O$) and sodium tetraphenylborate deposited upon silica particles from an alcohol solution by freeze-dry evaporation of said alcohol.

20. The catalyst of claim 19, wherein the alcohol is ethanol.

21. The catalyst of claim 19, wherein the molar ratio of Ni:DPPBA:tetraphenylborate is a 1:1:1.

22. The process of claim 19, wherein the loading of nickel on silica is between about 2 weight percent and about 4.5 weight percent.

23. The process of claim 19, wherein the loading of nickel on silica is about 3.4 weight percent.

24. The process of claim 19, wherein the alcohol solution is cooled to about −65° C. before freeze-dry evaporation of said alcohol.

* * * * *